(12) United States Patent
Lyu et al.

(10) Patent No.: US 8,217,195 B2
(45) Date of Patent: Jul. 10, 2012

(54) PHOTOCURABLE COMPOUND

(75) Inventors: Yi Yeol Lyu, Yongin-si (KR); Chul Ho Jeong, Gwangju (KR); Sun Jin Song, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 471 days.

(21) Appl. No.: 12/539,326

(22) Filed: Aug. 11, 2009

(65) Prior Publication Data

US 2010/0197876 A1 Aug. 5, 2010

(30) Foreign Application Priority Data

Feb. 3, 2009 (KR) .................. 10-2009-0008604

(51) Int. Cl.
*C07C 271/12* (2006.01)
(52) U.S. Cl. ...................................... 560/133
(58) Field of Classification Search .................. None
See application file for complete search history.

(56) References Cited

U.S. PATENT DOCUMENTS

2008/0138531 A1 6/2008 Laginess et al.
2008/0213585 A1 9/2008 Moroishi et al.

FOREIGN PATENT DOCUMENTS

KR 1020080060604 A 7/2008
WO 2006/071914 A2 7/2006

OTHER PUBLICATIONS

: Wang et al, Macromolecules, Synthesis and Sulfonation of Poly(arylethers) Containing Triphenyl Methane and Tetraphenyl Methane Moieties from Isocyanate-Masked Bisphenols, 2004, 37, pp. 3151-3158.*
Sengupta et al, Tetrahedron Letters, Synthetic Studies on Tetraphenylmethane Dendrimerrs, 1999, 40, pp. 9157-9161.*

* cited by examiner

*Primary Examiner* — Paul A Zucker
(74) *Attorney, Agent, or Firm* — Cantor Colburn LLP

(57) ABSTRACT

Disclosed is a compound having a photocurable urethane (meth)acrylate group, its manufacturing method, and a photocurable composition including the compound. The compound is represented by Chemical Formulae 1 to 6. Each of Chemical Formulae 1 to 6 includes a urethane (meth)acrylate group represented by Chemical Formula 1-1 or 1-2.

4 Claims, No Drawings

PHOTOCURABLE COMPOUND

CROSS-REFERENCE TO RELATED APPLICATION

This application claims priority to Korean Patent Application No. 10-2009-0008604, filed on Feb. 3, 2009, and all the benefits accruing therefrom under 35 U.S.C. §119, the contents of which in its entirety are herein incorporated by reference.

BACKGROUND

1. Field

This disclosure relates to a photocurable compound.

2. Description of the Related Art

Compounds including two or more reactive photocurable acrylate groups are used in various ways, for example, as photocurable adhesive resins, photocurable paints or inks, and the like. Photocurable acrylate groups form a crosslinked structure when they are polymerized by free-radical polymerization. Crosslinking changes various properties such resolution during exposure to light, solubility in a solvent, and the like. In particular, polymerization that generates radicals as a result of irradiation by light has been widely adopted due to the high reactivity of monomers, low cost, and excellent mechanical and optical properties of the final product.

SUMMARY

One aspect of the present invention provides a compound including a photocurable urethane (meth)acrylate group that is used for various photocurable radical polymerizations.

According to one aspect of the present invention, a novel compound represented by one of the following Chemical Formulae 1 to 6 is provided.

[Chemical Formula 1]

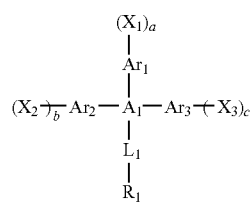

In the above Chemical Formula 1, $A_1$ is carbon (C) or silicon (Si), $Ar_1$ to Ara are independently a substituted or unsubstituted C6 to C20 arylene, where the substituted arylene is an arylene substituted with a C1 to C5 alkyl, $L_1$ is selected from the group consisting of a single bond and a C1 to C20 alkylene, $R_1$ is selected from the group consisting of hydrogen, a C1 to C5 alkyl, substituents represented by the following Chemical Formula 1-1 and substituents represented by the following Chemical Formula 1-2, and $X_1$ to $X_3$ are independently selected from the group consisting of hydrogen, a C1 to C5 alkyl, substituents represented by the following Chemical Formula 1-1 and substituents represented by the following Chemical Formula 1-2, provided that at least one of $R_1$ and $X_1$ to $X_3$ is selected from the group consisting of substituents represented by the following Chemical Formula 1-1 and substituents represented by the following Chemical Formula 1-2. In one embodiment, at least three of $R_1$ and $X_1$ to $X_3$ may be selected from the group consisting of substituents represented by the following Chemical Formula 1-1 and substituents represented by the following Chemical Formula 1-2. a to c in the Chemical Formula 1 are independently integers of 1 or 2, and when a to c are each equal to 2, each of $X_1$ to $X_3$ may be the same or different.

[Chemical Formula 1-1]

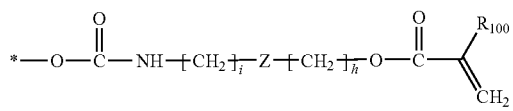

In the above Chemical Formula 1-1, Z is selected from the group consisting of a single bond, —O—, —COO—, and —OCO—, i is an integer ranging from 1 to 5, h is an integer ranging from 0 to 5, and $R_{100}$ is hydrogen or a methyl, provided that when Z is —O—, —COO—, or —OCO—, h is not zero (0).

[Chemical Formula 1-2]

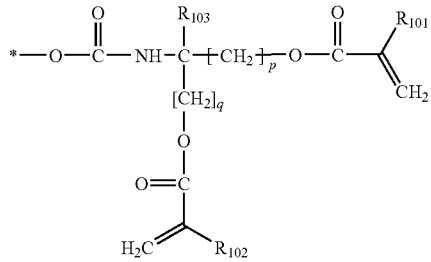

In the above Chemical Formula 1-2, p and q are independently an integer ranging from 1 to 5, and $R_{101}$ to $R_{103}$ are independently hydrogen or a methyl.

A compound of the above Chemical Formula 1 may include a compound represented by the following Chemical Formula 1A.

[Chemical Formula 1A]

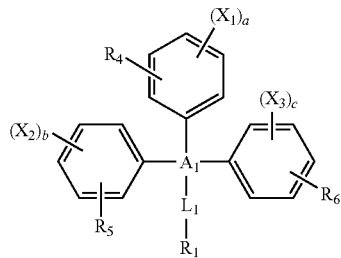

In the above Chemical Formula 1A, $A_1$ is carbon (C) or silicon (Si), $L_1$ is selected from the group consisting of a single bond and a C1 to C20 alkylene, $R_1$ is selected from the group consisting of hydrogen, a C1 to C5 alkyl, substituents represented by the above Chemical Formula 1-1 and substituents represented by the following Chemical Formula 1-2, and $R_1$, $R_4$ to $R_6$, and $X_1$ to $X_3$ are independently selected from the group consisting of hydrogen, a C1 to C5 alkyl, substituents represented by the above Chemical Formula 1-1 and substituents represented by the following Chemical Formula 1-2, provided that at least one of $R_1$, $R_4$ to $R_6$, and $X_1$ to $X_3$ is selected from the group consisting of substituents represented by the above Chemical Formula 1-1 and substituents represented by the following Chemical Formula 1-2. In one embodiment, at least three of $R_1$, $R_4$ to $R_6$, and $X_1$ to $X_3$ may be selected from the group consisting of substituents represented by the above Chemical Formula 1-1 and substituents represented by the following Chemical Formula 1-2. a to c in the Chemical Formula 1A are independently integers of 1 or 2, and when a to c are each equal to 2, each of $X_1$ to $X_3$ may be the same or different.

[Chemical Formula 2]

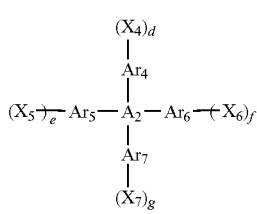

In the above Chemical Formula 2, $A_2$ is carbon (C) or silicon (Si), Ara to $Ar_7$ are independently a substituted or unsubstituted C6 to C20 arylene, where the substituted arylene is an arylene substituted with a C1 to C5 alkyl, and $X_4$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_4$ to $X_7$ is selected from the group consisting of substituents represented by the above Chemical Formula 1-1 and substituents represented by the following Chemical Formula 1-2. In one embodiment, at least three of $X_4$ to $X_7$ may be selected from the group consisting of substituents represented by the above Chemical Formula 1-1 and substituents represented by the following Chemical Formula 1-2. d to g in the Chemical Formula 2, are independently integers of 1 or 2, and when d to g are each equal to 2, each of $X_4$ to $X_7$ may be the same or different.

[Chemical Formula 2A]

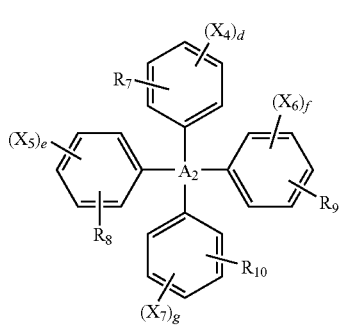

In the above Chemical Formula 2A, $A_2$ is carbon (C) or silicon (Si), and $R_7$ to $R_{10}$ and $X_4$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_7$ to $R_{10}$ and $X_4$ to $X_7$ is selected from the group consisting of substituents represented by the above Chemical Formula 1-1 and substituents represented by the following Chemical Formula 1-2. In one embodiment, at least three of $R_7$ to $R_{10}$ and $X_4$ to $X_7$ may be selected from the group consisting of substituents represented by the above Chemical Formula 1-1 and substituents represented by the following Chemical Formula 1-2. d to g in the Chemical Formula 2A, are independently integers of 1 or 2, and when d to g are each equal to 2, each of $X_4$ to $X_7$ may be the same or different.

[Chemical Formula 3]

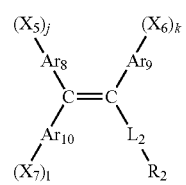

In the above Chemical Formula 3, $Ar_8$ to $Ar_{10}$ are the same or different and are independently a substituted or unsubstituted C6 to C20 arylene, where the substituted arylene is an arylene substituted with a C1 to C5 alkyl, $L_2$ is selected from the group consisting of a single bond and a C1 to C20 alkylene, $R_2$ is selected from the group consisting of hydrogen, a C1 to C5 alkyl, substituents represented by the above Chemical Formula 1-1 and substituents represented by the following Chemical Formula 1-2, and $X_5$ to $X_7$ are independently selected from the group consisting of hydrogen, a C1 to C5 alkyl, substituents represented by the above Chemical Formula 1-1 and substituents represented by the following Chemical Formula 1-2, provided that at least one of $R_2$ and $X_5$ to $X_7$ is selected from the group consisting of substituents represented by the above Chemical Formula 1-1 and substituents represented by the following Chemical Formula 1-2. In one embodiment, at least three of $R_2$ and $X_5$ to $X_7$ may be selected from the group consisting of substituents represented by the above Chemical Formula 1-1 and substituents represented by the following Chemical Formula 1-2. j, k, and l in Chemical Formula 3 are independently integers of 1 or 2, and when j, k, and l are each equal to 2, each of $X_5$ to $X_7$ may be the same or different.

The compound of the above Chemical Formula 3 may include a compound represented by the following Chemical Formula 3A.

[Chemical Formula 3A]

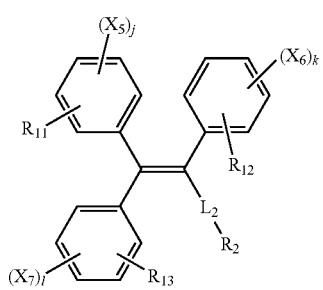

In the above Chemical Formula 3A, $L_2$ is selected from the group consisting of a single bond and a C1 to C20 alkylene, $R_2$ is selected from the group consisting of hydrogen, a C1 to C5 alkyl, substituents represented by the above Chemical Formula 1-1 and substituents represented by the following Chemical Formula 1-2, and $R_2$, $R_{11}$ to $R_{13}$, and $X_5$ to $X_7$ are independently selected from the group consisting of hydrogen, a C1 to C5 alkyl, substituents represented by the above Chemical Formula 1-1 and substituents represented by the following Chemical Formula 1-2, provided that at least one of $R_2$, $R_{11}$ to $R_{13}$, and $X_5$ to $X_7$ is selected from the group consisting of substituents represented by the above Chemical Formula 1-1 and substituents represented by the following Chemical Formula 1-2. In one embodiment, at least three of $R_2$, $R_{11}$ to $R_{13}$, and $X_5$ to $X_7$ may be selected from the group consisting of substituents represented by the above Chemical Formula 1-1 and substituents represented by the following Chemical Formula 1-2. j, k, and l in the Chemical Formula 4 are independently integers of 1 or 2, and when j, k, and l are each equal to 2, each of $X_5$ to $X_7$ may be the same or different.

[Chemical Formula 4]

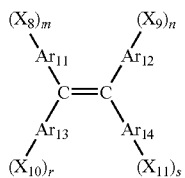

In the above Chemical Formula 4, $Ar_{11}$ to $Ar_{14}$ are the same or different and are independently a substituted or unsubstituted C6 to C20 arylene, where the substituted arylene is an arylene substituted with a C1 to C5 alkyl, and $X_8$ to $X_{11}$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_8$ to $X_{11}$ is selected from the group consisting of substituents represented by the above Chemical Formula 1-1 and substituents represented by the following Chemical Formula 1-2. In one embodiment, at least three of $X_8$ to $X_{11}$ may be selected from the group consisting of substituents represented by the above Chemical Formula 1-1 and substituents represented by the following Chemical Formula 1-2. m, n, r, and s in the Chemical Formula 4 are independently integers of 1 or 2, and when m, n, r, and s are each equal to 2, each of $X_8$ to $X_{11}$ may be the same or different.

The compound of the above Chemical Formula 4 may include a compound represented by the following Chemical Formula 4A.

[Chemical Formula 4A]

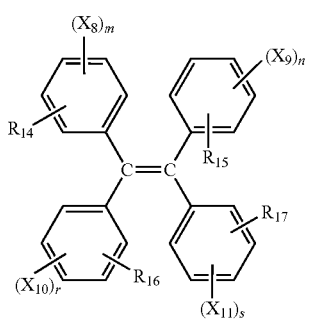

In the above Chemical Formula 4A, $R_{14}$ to $R_{17}$ and $X_{12}$ to $X_{15}$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_{14}$ to $R_{17}$ and $X_{12}$ to $X_{15}$ is selected from the group consisting of substituents represented by the above Chemical Formula 1-1 and substituents represented by the following Chemical Formula 1-2. In one embodiment, at least three of $R_{14}$ to $R_{17}$ and $X_{12}$ to $X_{15}$ may be selected from the group consisting of substituents represented by the above Chemical Formula 1-1 and substituents represented by the following Chemical Formula 1-2. m, n, r, and s in the Chemical Formula 4A are independently integers of 1 or 2, and when m, n, r, and s are each equal to 2, each of $X_8$ to $X_{11}$ may be the same or different.

[Chemical Formula 5]

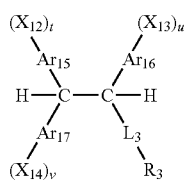

In the above Chemical Formula 5, $Ar_{15}$ to $Ar_{17}$ are the same or different and are independently a substituted or unsubstituted C6 to C20 arylene, where the substituted arylene is an arylene substituted with a C1 to C5 alkyl, $L_3$ is selected from the group consisting of a single bond and a C1 to C20 alkylene, $R_3$ is selected from the group consisting of hydrogen, a C1 to C5 alkyl, substituents represented by the above Chemical Formula 1-1 and substituents represented by the following Chemical Formula 1-2, and $X_{12}$ to $X_{14}$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_3$ and $X_{12}$ to $X_{14}$ is a substituent represented by the above Chemical Formula 1-1 and substituents represented by the following Chemical Formula 1-2. In one embodiment, at least three of $R_3$ and $X_{12}$ to $X_{14}$ may selected from the group consisting of substituents represented by the above Chemical Formula 1-1 and substituents represented by the following Chemical Formula 1-2. t, u, and v in the Chemical Formula 5 are independently integers of 1 or 2, and when t, u, and v are each equal to 2, each of $X_{12}$ to $X_{14}$ may be the same or different.

The compound of the above Chemical Formula 5 may include a compound represented by the following Chemical Formula 5A.

[Chemical Formula 5A]

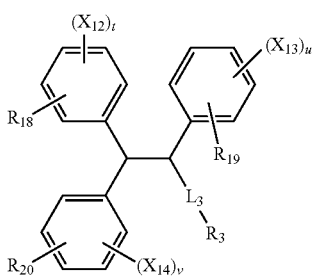

In the above Chemical Formula 5A, $L_3$ is selected from the group consisting of a single bond and a C1 to C20 alkylene, $R_3$ is selected from the group consisting of hydrogen, a C1 to C5 alkyl, substituents represented by the above Chemical Formula 1-1 and substituents represented by the following Chemical Formula 1-2, and $R_3$, $R_{18}$ to $R_{20}$, and $X_{12}$ to $X_{14}$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_3$, $R_{18}$ to $R_{20}$, and $X_{12}$ to $X_{14}$ is selected from the group consisting of substituents represented by the above Chemical Formula 1-1 and substituents represented by the following Chemical Formula 1-2. In one embodiment, at least three of $R_3$, $R_{18}$ to $R_{20}$, and $X_{12}$ to $X_{14}$ may be selected from the group consisting of substituents represented by the above Chemical Formula 1-1 and substituents represented by the following Chemical Formula 1-2. t, u, and v in the Chemical Formula 5A are independently integers of 1 or 2, and when t, u, and v are each equal to 2, each of $X_{12}$ to $X_{14}$ may be the same or different.

[Chemical Formula 6]

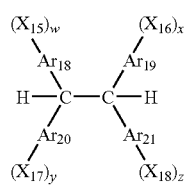

In the above Chemical Formula 6, $Ar_{18}$ to $Ar_{21}$ are the same or different and are independently a substituted or unsubstituted C6 to C20 arylene, where the substituted arylene is an arylene substituted with a C1 to C5 alkyl, and $X_{15}$ to $X_{18}$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_{15}$ to $X_{18}$ is selected from the group consisting of substituents represented by the above Chemical Formula 1-1 and substituents represented by the following Chemical Formula 1-2. In one embodiment, at least three of $X_{15}$ to $X_{18}$ may be selected from the group consisting of substituents represented by the above Chemical Formula 1-1 and substituents represented by the following Chemical Formula 1-2. w, x, y, and z in the Chemical Formula 6 are independently integers of 1 or 2, and when w, x, y, and z are each equal to 2, each of $X_{15}$ to $X_{18}$ may be the same or different.

The compound of the above Chemical Formula 6 may include a compound represented by the following Chemical Formula 6A.

[Chemical Formula 6A]

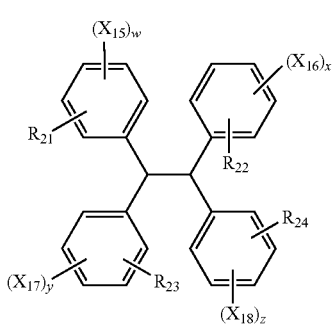

In the above Chemical Formula 6A, $R_{21}$ to $R_{24}$ and $X_{15}$ to $X_{18}$ are the same or different and are independently selected from the group consisting of hydrogen, a C1 to C5 alkyl, and substituents represented by the above Chemical Formula 1-1 and substituents represented by the following Chemical Formula 1-2, provided that at least one of $R_{21}$ to $R_{24}$ and $X_{15}$ to $X_{18}$ is selected from the group consisting of substituents represented by the above Chemical Formula 1-1 and substituents represented by the following Chemical Formula 1-2. In one embodiment, at least three of $R_{21}$ to $R_{24}$ and $X_{15}$ to $X_{18}$ may be selected from the group consisting of substituents represented by the above Chemical Formula 1-1 and substituents represented by the following Chemical Formula 1-2. w, x, y, and z in the Chemical Formula 6A are independently integers of 1 or 2, and when w, x, y, and z are each equal to 2, each of $X_{15}$ to $X_{18}$ may be the same or different.

Hereinafter, further aspects of the present invention will be described in detail.

DETAILED DESCRIPTION

The present invention will be described more fully hereinafter in the following detailed description of the invention, in which some but not all embodiments of the invention are described. This invention may be embodied in many different forms and is not construed as limited to the embodiments set forth herein; rather, these embodiments are provided so that this disclosure will satisfy applicable legal requirements.

As used herein, the terms "a" and "an" are open terms that may be used in conjunction with singular items or with plural items.

The use of the terms such as "a to d" used below with reference to Chemical Formula 1 and other similar expressions used with reference to other Chemical Formulae are meant to imply "a, b, c and d". The term "single bond" implies that the particular substitutent is "optional".

For example, the statement "$L_9'$ to $L_{12}'$ are independently selected from the group consisting of a single bond, and a C1 to C20 substituted or unsubstituted alkylene" implies that $L_9'$ to $L_{12}'$ are optional and may not be present. In the event that a particular substitutent is absent then the core atom will be covalently bonded to a terminal atom in a given structure depicted in this disclosure.

The term "and/or" is used to imply both "and" and "or". For example, the statement that "X includes A and/or B" implies that X may include, A, B, or a combination of A and B. Similarly, the statement that "X is selected from the group consisting of A and/or B" implies that X may be selected from the group consisting of A, B, or a combination of A and B.

As used herein, the term "(meth)acrylate" refers to both acrylate and methacrylate, and the term "(meth)acryloyl" refers to both acryloyl and meth)acryloyl.

According to one embodiment of the present invention, a compound represented by Chemical Formulae 1 to 6 is provided.

[Chemical Formula 1]

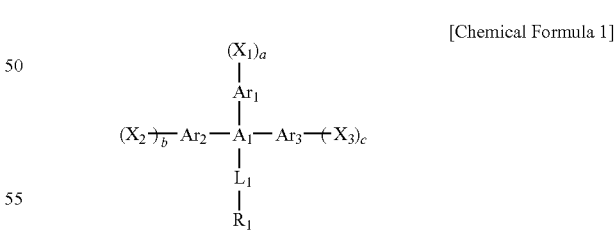

In the above Chemical Formula 1, $A_1$ is carbon (C) or silicon (Si), $Ar_1$ to Ara are the same or different and are independently a substituted or unsubstituted C6 to C20 arylene, where the substituted arylene is an arylene substituted with a C1 to C5 alkyl, $L_1$ is selected from the group consisting of a single bond and a C1 to C20 alkylene, $R_1$ is selected from the group consisting of hydrogen, a C1 to C5 alkyl, and substituents represented by the above Chemical Formula 1-1 and substituents represented by the following Chemical Formula 1-2, and $X_1$ to $X_3$ are the same or different and are selected from the group consisting of hydrogen, a C1 to C5 alkyl, substituents represented by the above Chemical Formula 1-1 and substituents represented by the following Chemical Formula 1-2, provided that at least one of $R_1$ and $X_1$ to $X_3$ is selected from the group consisting of substituents represented by the above Chemical Formula 1-1 and substituents represented by the following Chemical Formula 1-2. In one embodiment, at least three of $R_1$ and $X_1$ to $X_3$ may be selected from the group consisting of substituents represented by the above Chemical Formula 1-1 or 1-2. a to c in the Chemical Formula 1 are independently integers of 1 or 2, and when a to c are each equal to 2, each of $X_1$ to $X_3$ may be the same or different.

[Chemical Formula 1-1]

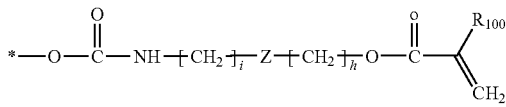

In the above Chemical Formula 1-1, Z is selected from the group consisting of a single bond, —O—, —COO—, and —OCO—, i is an integer ranging from 1 to 5, h is an integer ranging from 0 to 5, and $R_{100}$ is hydrogen or a methyl, provided that when Z is —O—, —COO—, or —OCO—, h is not zero (0).

[Chemical Formula 1-2]

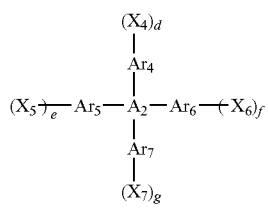

In the above Chemical Formula 1-2, p and q are independently an integer ranging from 1 to 5, and $R_{101}$ to $R_{103}$ are independently hydrogen or a methyl.

A compound of the above Chemical Formula 1 may be represented by the following Chemical Formula 1A.

[Chemical Formula 1A]

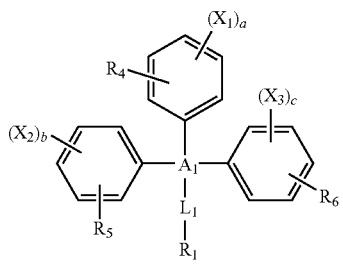

In the above Chemical Formula 1A, $A_1$ is carbon (C) or silicon (Si), $L_1$ is selected from the group consisting of a single bond and a C1 to C20 alkylene, $R_1$ is selected from the group consisting of hydrogen, a C1 to C5 alkyl, substituents represented by the above Chemical Formula 1-1 and substituents represented by the following Chemical Formula 1-2, and $R_1$, $R_4$ to $R_6$, and $X_1$ to $X_3$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_1$, $R_4$ to $R_6$, and $X_1$ to $X_3$ is selected from the group consisting of substituents represented by the above Chemical Formula 1-1 and substituents represented by the following Chemical Formula 1-2. In one embodiment, at least three of $R_1$, $R_4$ to $R_6$, and $X_1$ to $X_3$ may be selected from the group consisting of substituents represented by the above Chemical Formula 1-1 and substituents represented by the following Chemical Formula 1-2. a to c in the Chemical Formula 1A are independently integers of 1 or 2, and when a to c are each equal to 2, each of $X_1$ to $X_3$ may be the same or different.

[Chemical Formula 2]

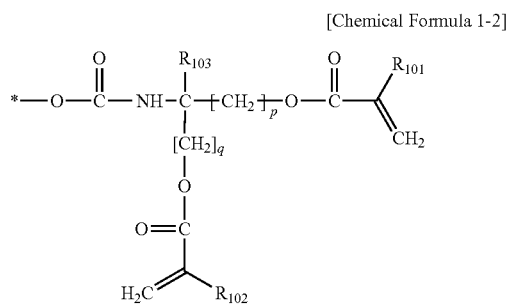

In the above Chemical Formula 2, $A_2$ is carbon (C) or silicon (Si), $Ar_4$ to $Ar_7$ are the same or different and are independently a substituted or unsubstituted C6 to C20 arylene, where the substituted arylene is an arylene substituted with a C1 to C5 alkyl, and $X_4$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_4$ to $X_7$ is selected from the group consisting of substituents represented by the above Chemical Formula 1-1 and substituents represented by the following Chemical Formula 1-2. In one embodiment, at least three of $X_4$ to $X_7$ may be selected from the group consisting of substituents represented by the above Chemical Formula 1-1 and substituents represented by the following Chemical Formula 1-2. d to g in the Chemical Formula 2 are independently integers of 1 or 2, and when d to g are each equal to 2, each of $X_4$ to $X_7$ may be the same or different.

The compound of the above Chemical Formula 2 may include a compound represented by the following Chemical Formula 2A.

[Chemical Formula 2A]

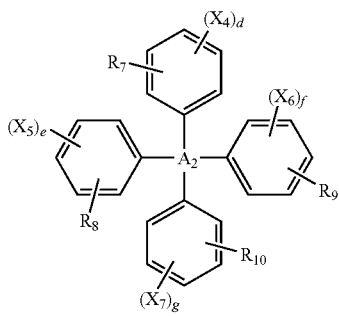

In the above Chemical Formula 2A, $A_2$ is carbon (C) or silicon (Si), and $R_7$ to $R_{10}$ and $X_4$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_7$ to $R_{10}$ and $X_4$ to $X_7$ is selected from the group consisting of substituents represented by the above Chemical Formula 1-1 and substituents represented by the following Chemical Formula 1-2. In one embodiment, at least three of $R_7$ to $R_{10}$ and $X_4$ to $X_7$ may be selected from the group consisting of substituents represented by the above Chemical Formula 1-1 and substituents represented by the following Chemical Formula 1-2. d to g in the Chemical Formula 2A are independently integers of 1 or 2, and when d to g are each equal to 2, each of $X_4$ to $X_7$ may be the same or different.

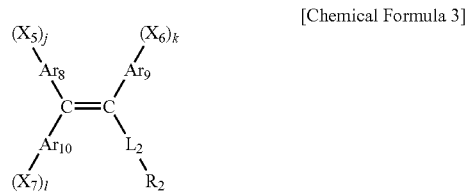

[Chemical Formula 3]

In the above Chemical Formula 3, $Ar_8$ to $Ar_{10}$ are the same or different and are independently a substituted or unsubstituted C6 to C20 arylene, where the substituted arylene is an arylene substituted with a C1 to C5 alkyl, $L_2$ is selected from the group consisting of a single bond and a C1 to C20 alkylene, $R_2$ is selected from the group consisting of hydrogen, a C1 to C5 alkyl, substituents represented by the above Chemical Formula 1-1 and substituents represented by the following Chemical Formula 1-2, and $X_5$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_2$ and $X_5$ to $X_7$ is selected from the group consisting of substituents represented by the above Chemical Formula 1-1 and substituents represented by the following Chemical Formula 1-2. In one embodiment, at least three of $R_2$ and $X_5$ to $X_7$ may be selected from the group consisting of substituents represented by the above Chemical Formula 1-1 and substituents represented by the following Chemical Formula 1-2. j, k, and l in the Chemical Formula 3 are independently integers of 1 or 2, and when j, k, and l are each equal to 2, each of $X_5$ to $X_7$ may be the same or different.

The compound of the above Chemical Formula 3 may be represented by the following Chemical Formula 3A.

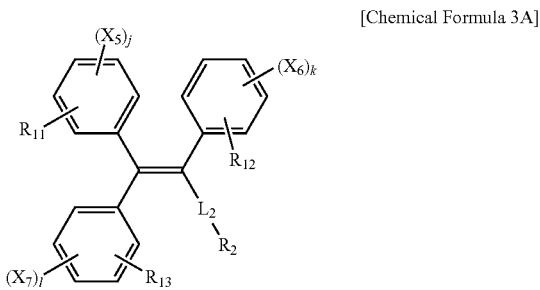

[Chemical Formula 3A]

In the above Chemical Formula 3A, $L_2$ is selected from the group consisting of a single bond and a C1 to C20 alkylene, $R_2$ is selected from the group consisting of hydrogen, a C1 to C5 alkyl, substituents represented by the above Chemical Formula 1-1 and substituents represented by the following Chemical Formula 1-2, and $R_2$, $R_{11}$ to $R_{13}$, and $X_5$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_2$, $R_{11}$ to $R_{13}$, and $X_5$ to $X_7$ is selected from the group consisting of substituents represented by the above Chemical Formula 1-1 and substituents represented by the following Chemical Formula 1-2. In one embodiment, at least three of $R_2$, $R_{11}$ to $R_{13}$, and $X_5$ to $X_7$ may be selected from the group consisting of substituents represented by the above Chemical Formula 1-1 and substituents represented by the following Chemical Formula 1-2. j, k, and l in the Chemical Formula 3A are independently integers of 1 or 2, and when j, k, and l are each equal to 2, each of $X_5$ to $X_7$ may be the same or different.

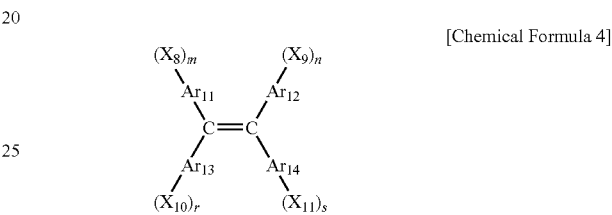

[Chemical Formula 4]

In the above Chemical Formula 4, $Ar_{11}$ to $Ar_{14}$ are the same or different and are independently a substituted or unsubstituted C6 to C20 arylene, where the substituted arylene is an arylene substituted with a C1 to C5 alkyl, and $X_8$ to $X_{11}$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_8$ to $X_{11}$ is selected from the group consisting of substituents represented by the above Chemical Formula 1-1 and substituents represented by the following Chemical Formula 1-2. In one embodiment, at least three of $X_8$ to $X_{11}$ may be selected from the group consisting of substituents represented by the above Chemical Formula 1-1 and substituents represented by the following Chemical Formula 1-2. m, n, r, and s in the Chemical Formula 4 are independently integers of 1 or 2, and when m, n, r, and s are each equal to 2, each of $X_8$ to $X_{11}$ may be the same or different.

The compound of the above Chemical Formula 4 may be represented by the following Chemical Formula 4A.

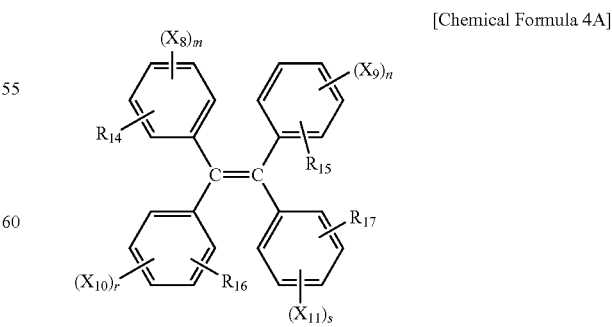

[Chemical Formula 4A]

In the above Chemical Formula 4A, $R_{14}$ to $R_{17}$ and $X_{12}$ to $X_{15}$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_{14}$ to $R_{17}$ and $X_{12}$ to $X_{15}$ is selected from the group consisting of substituents represented by the above Chemical Formula 1-1 and substituents represented by the following Chemical Formula 1-2. In one embodiment, at least three of $R_{14}$ to $R_{17}$ and $X_{12}$ to $X_{15}$ may be selected from the group consisting of substituents represented by the above Chemical Formula 1-1 and substituents represented by the following Chemical Formula 1-2. m, n, r, and s in the Chemical Formula 4A are independently integers of 1 or 2, and when m, n, r, and s are each equal to 2, each of $X_8$ to $X_{11}$ may be the same or different.

[Chemical Formula 5]

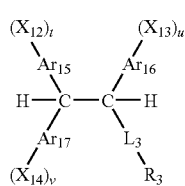

In the above Chemical Formula 5, $Ar_{15}$ to $Ar_{17}$ are the same or different and are independently a substituted or unsubstituted C6 to C20 arylene, where the substituted arylene is an arylene substituted with a C1 to C5 alkyl, $L_3$ is selected from the group consisting of a single bond and a C1 to C20 alkylene, $R_3$ is selected from the group consisting of hydrogen, a C1 to C5 alkyl, substituents represented by the above Chemical Formula 1-1 and substituents represented by the following Chemical Formula 1-2, and $X_{12}$ to $X_{14}$ are independently selected from the group consisting of hydrogen, a C1 to C5 alkyl, substituents represented by the above Chemical Formula 1-1 and substituents represented by the following Chemical Formula 1-2, provided that at least one of $R_3$ and $X_{12}$ to $X_{14}$ is a substituent represented by the above Chemical Formula 1-1 and substituents represented by the following Chemical Formula 1-2. In one embodiment, at least three of $R_3$ and $X_{12}$ to $X_{14}$ may be selected from the group consisting of substituents represented by the above Chemical Formula 1-1 and substituents represented by the following Chemical Formula 1-2. t, u, and v in the Chemical Formula 5 are independently integers of 1 or 2, and when t, u, and v are each equal to 2, each of $X_{12}$ to $X_{14}$ may be the same or different.

The compound of the above Chemical Formula 5 is represented by the following Chemical Formula 5A.

[Chemical Formula 5A]

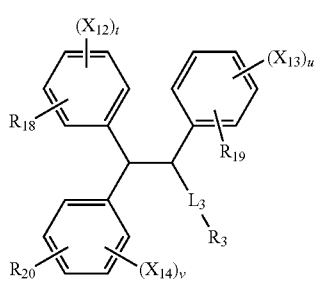

In the above Chemical Formula 5A, $L_3$ is selected from the group consisting of a single bond and a C1 to C20 alkylene, $R_3$ is selected from the group consisting of hydrogen, a C1 to C5 alkyl, substituents represented by the above Chemical Formula 1-1 and substituents represented by the following Chemical Formula 1-2, and $R_3$, $R_{18}$ to $R_{20}$, and $X_{12}$ to $X_{14}$ are independently selected from the group consisting of hydrogen, a C1 to C5 alkyl, and substituents represented by the above Chemical Formula 1-1 and substituents represented by the following Chemical Formula 1-2, provided that at least one of $R_3$, $R_{18}$ to $R_{20}$, and $X_{12}$ to $X_{14}$ is selected from the group consisting of substituents represented by the above Chemical Formula 1-1 and substituents represented by the following Chemical Formula 1-2. In one embodiment, at least three of $R_3$, $R_{18}$ to $R_{20}$, and $X_{12}$ to $X_{14}$ may be selected from the group consisting of substituents represented by the above Chemical Formula 1-1 and substituents represented by the following Chemical Formula 1-2. t, u, and v in the Chemical Formula 5A are independently integers of 1 or 2, and when t, u, and v are each equal to 2, each of $X_{12}$ to $X_{14}$ may be the same or different.

[Chemical Formula 6]

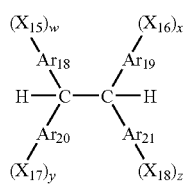

In the above Chemical Formula 6, $Ar_{18}$ to $Ar_{21}$ are the same or different and are independently a substituted or unsubstituted C6 to C20 arylene, where the substituted arylene is an arylene substituted with a C1 to C5 alkyl, and $X_{15}$ to $X_{18}$ are the same or different and are independently selected from the group consisting of hydrogen, a C1 to C5 alkyl, substituents represented by the above Chemical Formula 1-1 and substituents represented by the following Chemical Formula 1-2, provided that at least one of $X_{15}$ to $X_{18}$ is selected from the group consisting of substituents represented by the above Chemical Formula 1-1 and substituents represented by the following Chemical Formula 1-2. In one embodiment, at least three of $X_{15}$ to $X_{18}$ may be selected from the group consisting of substituents represented by the above Chemical Formula 1-1 and substituents represented by the following Chemical Formula 1-2. w, x, y, and z are independently integers of 1 or 2, and when w, x, y, and z are each equal to 2, each of $X_{15}$ to $X_{18}$ may be the same or different.

The compound of the above Chemical Formula 6 is represented by the following Chemical Formula 6A.

[Chemical Formula 6A]

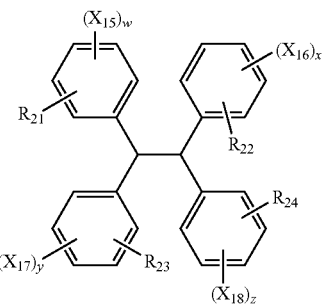

In the above Chemical Formula 6A, $R_{21}$ to $R_{24}$ and $X_{15}$ to $X_{18}$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_{21}$ to $R_{24}$ and $X_{15}$ to $X_{18}$ is selected from the group consisting of substituents represented by the above Chemical Formula 1-1 and substituents represented by the following Chemical Formula 1-2. In one embodiment, at least three of $R_{21}$ to $R_{24}$ and $X_{15}$ to $X_{18}$ may be selected from the group consisting of substituents represented by the above Chemical Formula 1-1 and substituents represented by the following Chemical Formula 1-2. w, x, y, and z in the Chemical Formula 6A, are independently integers of 1 or 2, and when w, x, y, and z are each equal to 2, each of $X_{15}$ to $X_{18}$ may be the same or different.

The compound including a photocurable urethane (meth) acrylate group has an aromatic structure in the center thereof, and thus has a strong internal skeletal structure, and includes a photocurable urethane (meth)acrylate group having a long branch chain as an aromatic structural substituent. Accordingly, it may be usefully applied for photo-initiative radical polymerization.

Hereinafter, a method of manufacturing a compound including the photocurable urethane (meth)acrylate group is illustrated.

The compound may be prepared by reacting one of the compounds having a reactive group and represented by the following Chemical Formula 7 to 12 with a (meth)acryloyl isocyanate derivative represented by Chemical Formula 13 or 14. This urethane reaction may be performed at a temperature of about 30 to about 100° C.

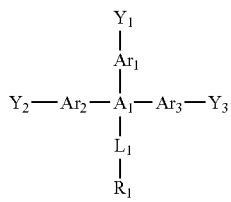

[Chemical Formula 7]

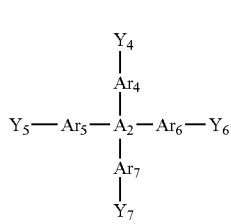

[Chemical Formula 8]

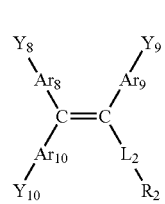

[Chemical Formula 9]

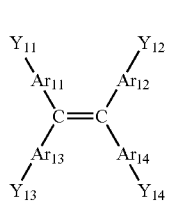

[Chemical Formula 10]

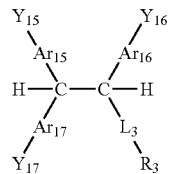

[Chemical Formula 11]

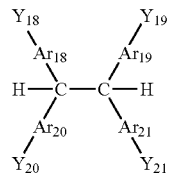

[Chemical Formula 12]

In the above Chemical Formulae 7 to 12, $A_1$ and $A_2$ are carbon (C) or silicon (Si), $L_1$ to $L_3$ are independently selected from the group consisting of a single bond and a C1 to C20 alkylene, $R_1$ to $R_3$ are independently selected from the group consisting of hydrogen, a C1 to C5 alkyl, substituents represented by the above Chemical Formula 1-1 and substituents represented by the following Chemical Formula 1-2, $Ar_1$ to $Ar_{21}$ are the same or different and are independently a substituted or unsubstituted C6 to C20 arylene, where the substituted arylene is an arylene substituted with a C1 to C5 alkyl, and $Y_1$ to $Y_{21}$ are the same or different and are independently a reactive group selected from the group consisting of a hydroxy, an amine, and combinations thereof.

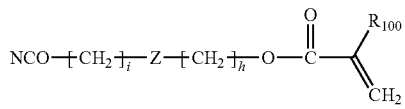

[Chemical Formula 13]

In the above Chemical Formula 13, Z is selected from the group consisting of a single bond, —O—, —COO—, and —OCO—, i is an integer ranging from 1 to 5, h is an integer ranging from 0 to 5, and $R_{100}$ is hydrogen or a methyl, provided that when Z is —O—, —COO—, or —OCO—, h is not zero (0).

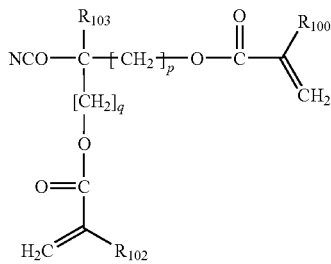

[Chemical Formula 14]

In the above Chemical Formula 14, p and q are independently an integer ranging from 1 to 5, and $R_{101}$ to $R_{103}$ are independently hydrogen or a methyl.

Examples of the compound represented by the above Chemical Formula to 12 include 1,1,1-tris(4-hydroxyphenyl)

methane, 1,1,1-tris(4-hydroxyphenyl)ethane, 1,1,1-tris(4-hydroxyphenyl)propane, 1,1,1-tris(4-hydroxyphenyl)butane, 1,1,1-tris(4-hydroxyphenyl)pentane, 1,1,1-tris(4-hydroxyphenyl)silane, 1,1,2-(4-hydroxyphenyl)ethene, tetrakis(p-hydroxyphenyl)methane, tetrakis(p-hydroxyphenyl)ethane, tetrakis(p-hydroxyphenyl)ethene, tetrakis(p-hydroxyphenyl)silane, or the like, or combinations including at least one of the foregoing.

Examples of acryloyl or methacryloyl isocyanate derivatives represented by the Chemical Formulas 13 or 14 above include (meth)acryloyloxymethyl isocyanate, (meth)acryloyloxyethyl isocyanate, (meth)acryloyloxypropyl isocyanate, (meth)acryloyloxybutyl isocyanate, (meth)acryloyloxypentyl isocyanate, isocyanatomethyl(meth)acrylate, isocyanatoethyl(meth)acrylate, isocyanatopropyl(meth)acrylate, isocyanatobutyl(meth)acrylate, isocyanatopentyl(meth)acrylate, 1,1-bis((meth)acryloyloxymethyl)methyl isocyanate, 1,1-bis((meth)acryloyloxymethyl)ethyl isocyanate, 1,1-bis((meth)acryloyloxymethyl)propyl isocyanate, 1,1-bis((meth)acryloyloxymethyl)butyl isocyanate, 1,1-bis((meth)acryloyloxymethyl)pentyl isocyanate, or the like, or a combination including at least one of the foregoing acryloyl or methacryloyl isocyanate derivatives.

The urethane reaction may further include a catalyst. The catalyst includes an organic tin compound, a tertiary amine aprotic salt, and the like, for example dibutyl tin dilaurate, dibutyl tin diacetate, dibutyl tin dimercaptide, triethylenediamine, 1,4-diazabicyclo[2,2,2]octane, or the like. The compound including a photocurable urethane (meth)acrylate group may be used to manufacture an adhesive composition, photocurable paint and ink compositions, a light guide, an insulation layer, an optical filter, a flame retardant resin, a plastic optical fiber, and the like.

The following examples illustrate the present invention in more detail. However, it is understood that the present invention is not limited by these examples.

Example 1

Synthesis of a Compound of Chemical Formula A

Example 1-1

Synthesis of a Compound of Chemical Formula (f)

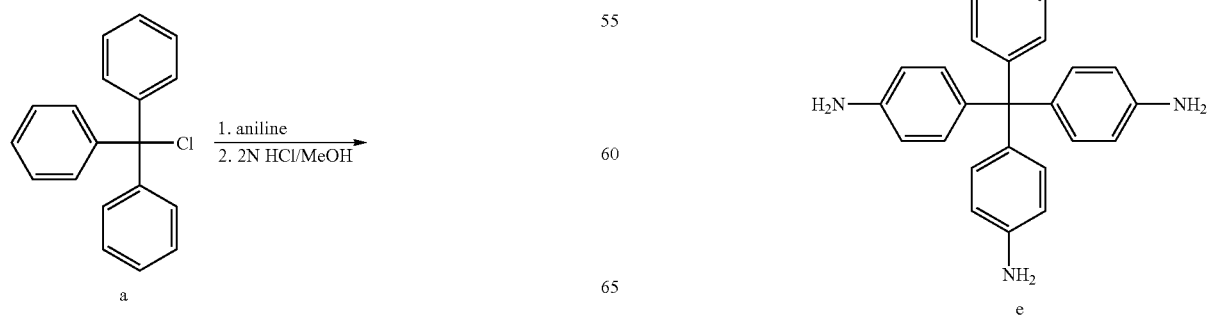

-continued

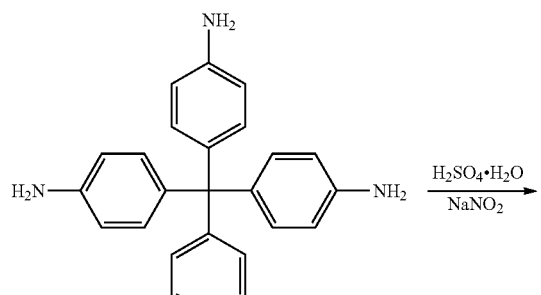

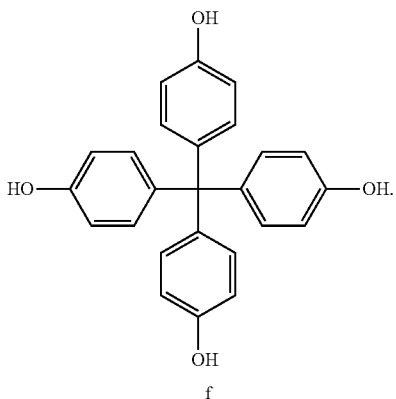

Referring to Reaction Scheme 1, a compound of Chemical Formula f is prepared by adding 750 grams ("g") (2.69 moles ("mol")) of a compound of Chemical Formula a and 678 g (7.28 mol) of aniline in a 10000 milliliter ("ml") round flask, heating the mixture to 200° C. while agitating it, and cooling it to 90° C. Then, 4100 ml of HCl and 3100 ml of methanol are added thereto. The resulting mixture is refluxed for 1 hour. The prepared solid material is filtrated and washed with 300 ml of methanol, and then added to 5000 ml of ethanol. While the mixture is agitated, 816 ml of sulfuric acid is slowly added in a dropwise fashion. The resulting mixture is cooled to −10° C., and 610 ml of isoamyl nitrile is slowly added thereto in a dropwise fashion. The resulting mixture is agitated for one hour. While maintaining its temperature, 1220 ml of phosphorous acid is added to the resulting mixture. The resulting product is heated and then refluxed and agitated for one hour, obtaining 700 g of a compound of Chemical Formula c ($^1$H NMR (300 MHz, CDCl$_3$), δ 7.18-7.25 (m, 20H)).

After adding 2750 ml of nitric acid and cooling to −10° C., 550 g (1.71 mol) of the compound of Chemical Formula c is slowly added thereto. Then, 1830 ml of acetic acid anhydride is slowly added thereto in a dropwise fashion. Then, 3660 ml of acetic acid is added to the above mixture, and the resulting product is agitated for one hour and filtrated, and then washed, obtaining 335 g of a compound of Chemical Formula d ($^1$H NMR (300 MHz, DMSO) δ 7.59 (d, 8H), 8.22 (d, 8H)).

Then, 4500 ml of tetrahydrofuran is added in a hydrogenizing reactor, and 450 g (0.89 mol) of the compound of Chemical Formula d is added thereto. On the other hand, 90 g of a palladium/carbon catalyst is added to 1200 ml of ethanol. This mixture is slowly added to the reactor. The resulting product is agitated for 30 hours while hydrogen gas is continuously injected into the reactor. Then, it is washed with ethanol and n-hexane and dried, obtaining 295 g of a compound of Chemical Formula e ($^1$H NMR (300 MHz, DMSO) δ 4.83 (s, 8H), 6.37 (d, 8H), 6.66 (d, 8H)).

400 g (1.05 mol) of the compound of Chemical Formula e is added to 1200 in of ultrapure water. The mixture is added to 320 ml of sulfuric acid while agitating it. Then, sodium nitrite is added thereto in a dropwise fashion at 0° C., and the resulting product is agitated at 50° C., obtaining tetrakis(p-hydroxyphenyl)methane (a compound of Chemical Formula f) (1H NMR (300 MHz, DMSO) δ 6.60 (d, 8H), 6.80 (d, 8H), 9.25 (s, 4H)).

Example 1-2

Synthesis of a Compound of Chemical Formula A

[Reaction Scheme 2]

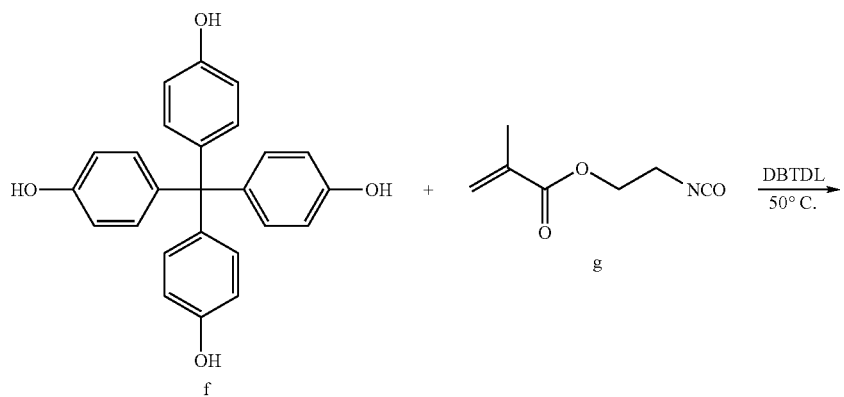

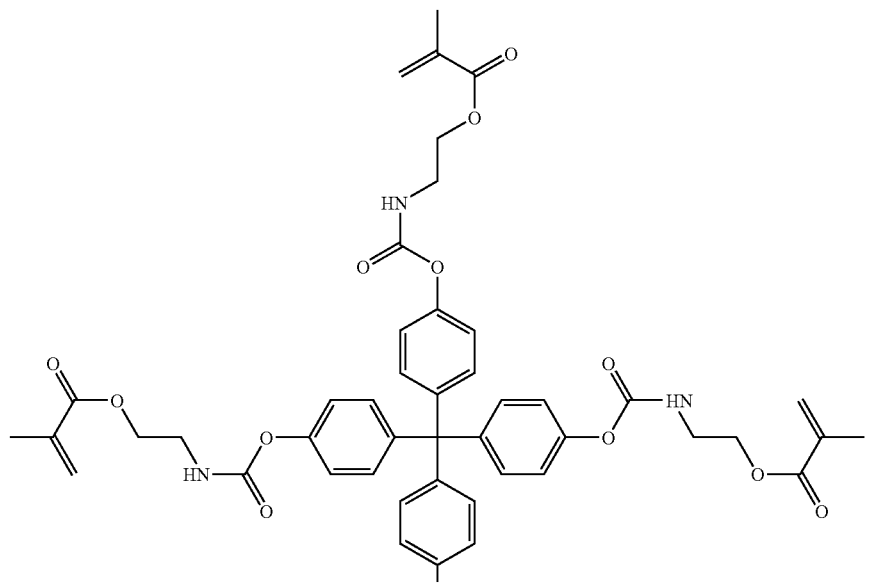

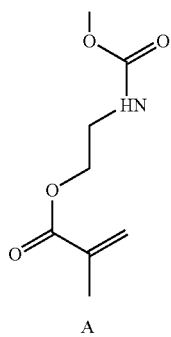

A

Referring to Reaction Scheme 2, 38.42 g (0.1 mol) of tetrakis(p-hydroxyphenyl)methane (the compound of Chemical Formula f) is dissolved in 500 ml of ethyl acetate, and then methacryloyl oxyethyl isocyanate and 65.16 g (0.42 mol) of the compound of Chemical Formula g are reacted together at 50° C. for 15 hours by using 6.63 g (0.0105 mol) of dibutyl tin dilaurate (DBTDL) as a catalyst, synthesizing a compound of Chemical Formula A ($^1$H NMR (300 MHz, CDCl$_3$) δ 8.08 (t NH), 6.7-6.9 (d 8H), 6.8-7.0 (d 8H), 5.94, 5.45 (s C=CH$_2$), 4.00 (t CH$_2$), 3.29 (t CH$_2$), 1.78 (s CH$_3$)).

Example 2

Synthesis of a Compound of Chemical Formula B

A compound of the following Chemical Formula B ($^1$H NMR (300 MHz, CDCl$_3$) δ 8.08 (t NH), 6.7-6.9 (d 8H), 6.8-7.0 (d 8H), 5.94, 5.45 (s C=CH$_2$), 6.03 (s 4H), 4.00 (t CH$_2$), 3.29 (t CH$_2$)) is prepared according to the same method as in Example 1, except for using isocyanatoethyl acrylate instead of methacryloyl oxyethyl isocyanate.

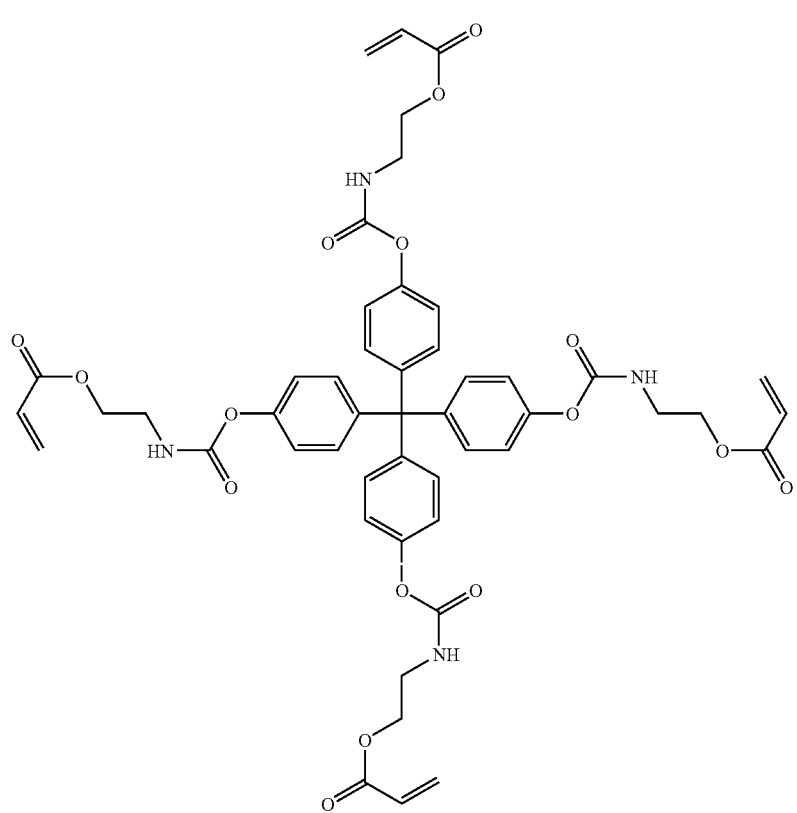
Example 3
Synthesis of a Compound of Chemical Formula C
A compound of the following Chemical Formula B ($^1$H NMR (300 MHz, CDCl$_3$) δ 8.03 (s NH), 6.9-7.1 (d 8H), 7.1-7.3 (d 8H), 6.27, 5.59 (s C=CH$_2$), 6.05 (s 6H), 4.71 (s CH$_2$), 1.57 (s CH$_3$)) is prepared according to the same method as in Example 1, except for using 1,1-bis(acryloyloxymethyl)ethyl isocyanate instead of methacryloyl oxyethyl isocyanate.
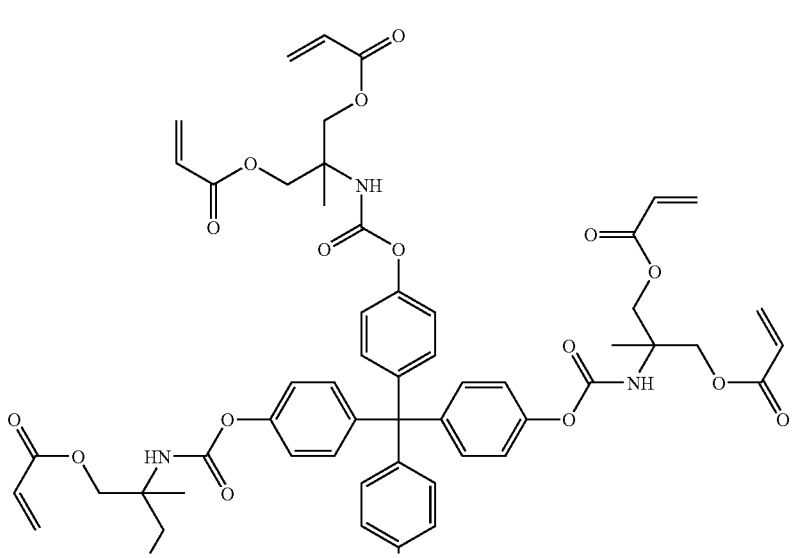

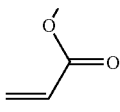
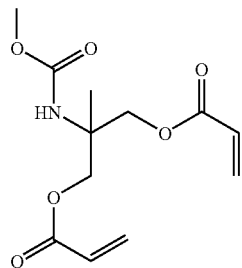

Example 4

Synthesis of a Compound of Chemical Formula D

A compound of the following Chemical Formula D ($^1$H NMR (300 MHz, CDCl$_3$) δ 8.22 (t NH) δ 6.9-7.0 (d 6H), 7.0-7.1 (d 6H), 6.13, 5.59 (s C=CH$_2$), 4.26 (t CH$_2$), 3.56 (t CH$_2$), 1.91 (s CH$_3$)) is prepared according to the same method as in Example 1, except for using 1,1,1-tris(4-hydroxyphenyl)ethane instead of tetrakis(p-hydroxyphenyl)methane.

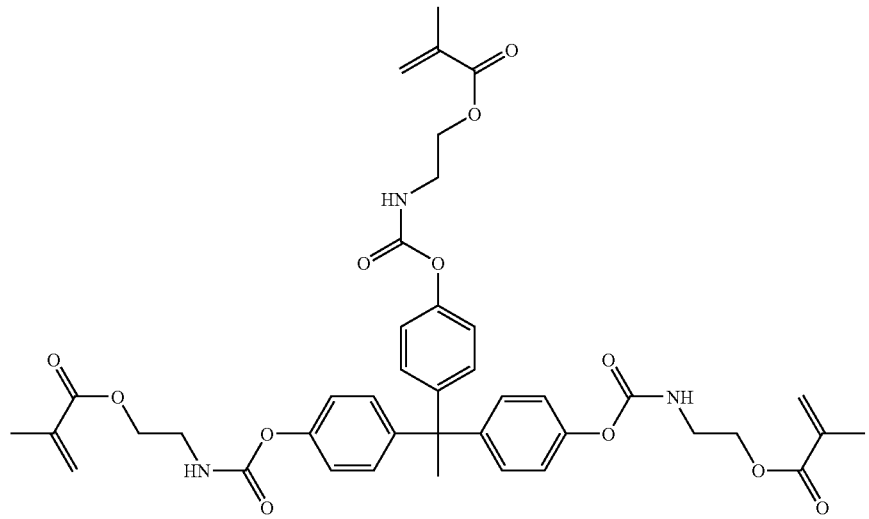

D

Example 5

Synthesis of a Compound of Chemical Formula E

A compound of the following Chemical Formula E ($^1$H NMR (300 MHz, CDCl$_3$) δ 8.20 (t NH), 6.7-6.9 (d 8H), 6.8-7.0 (d 8H), 5.94, 5.45 (s C=CH$_2$), 6.08 (s 3H), 4.00 (t CH$_2$), 3.29 (t CH$_2$), 1.88 (s CH$_3$)) is prepared according to the same method as in Example 1, except for using 1,1,1-tris(4-hydroxyphenyl)ethane instead of tetrakis(p-hydroxyphenyl)methane and isocyanatoethyl acrylate instead of methacryloyl oxyethyl isocyanate.

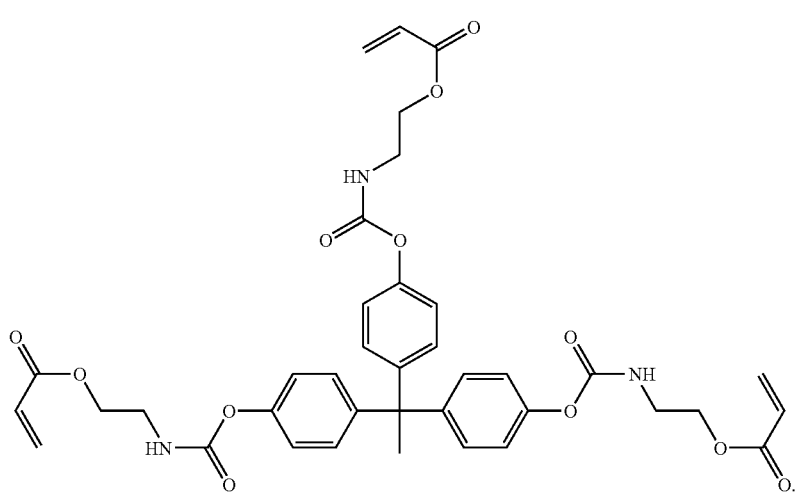

E

Example 6

Synthesis of a Compound of Chemical Formula F

A compound of the following Chemical Formula F ($^1$H NMR (300 MHz, CDCl$_3$) δ 8.03 (sNH), 6.9-7.1 (d 8H), 7.1-7.3 (d 8H), 6.27, 5.59 (s C=CH$_2$), 6.05 (s 6H), 4.73 (s CH$_2$), 1.91 (s CH$_3$), 1.57 (s CH$_3$)) is prepared according to the same method as in Example 1, except for using 1,1,1-tris(4-hydroxyphenyl)ethane instead of tetrakis(p-hydroxyphenyl)methane and 1,1-bis(acryloyloxymethyl)ethyl isocyanate instead of methacryloyl oxyethyl isocyanate.

Example 7

Synthesis of a Compound of Chemical Formula G

A compound of the following Chemical Formula G ($^1$H NMR (300 MHz, CDCl$_3$) δ 8.08 (t NH), 7.0-7.2 (d 8H), 7.2-7.4 (d 8H), 6.48, 6.40 (s C=CH$_2$), 4.58 (t CH$_2$), 3.15 (t CH$_2$), 2.01 (s CH$_3$)) is prepared according to the same method as in Example 1, except for using tetrakis(p-hydroxyphenyl)ethene instead of tetrakis(p-hydroxyphenyl)methane.

F

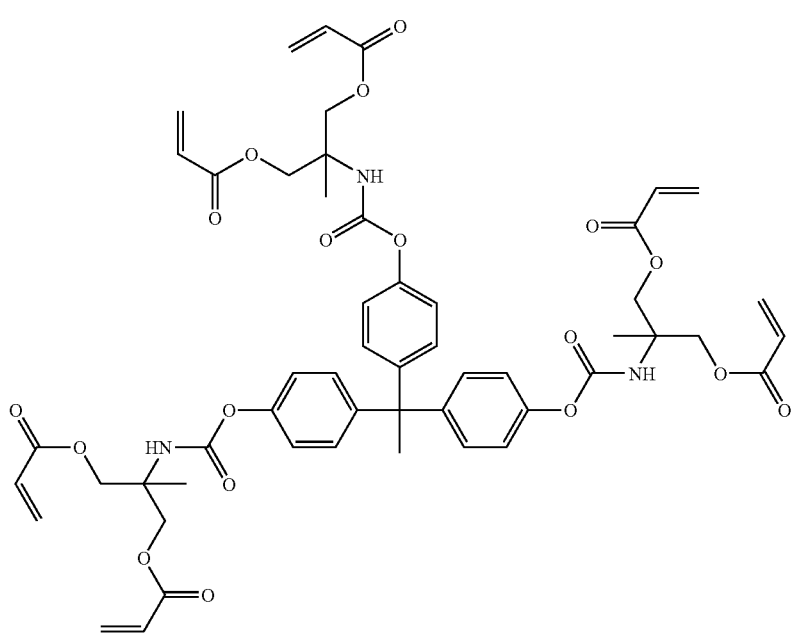

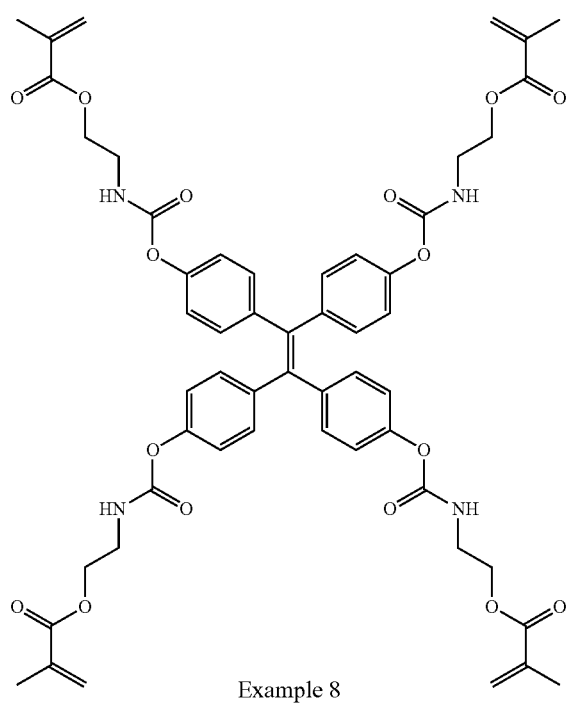

Example 8

Synthesis of a Compound of Chemical Formula H

A compound of the following Chemical Formula H ($^1$H NMR (300 MHz, CDCl$_3$) δ 8.03 (t NH), 7.0-7.2 (d 8H), 7.2-7.4 (d 8H), 6.27, 5.59 (s C=CH$_2$), 6.05 (s 3H), 4.58 (t CH$_2$), 3.15 (t CH$_2$), 2.01 (s CH$_3$)) is prepared according to the same method as in Example 1-2, except for using tetrakis(p-hydroxyphenyl)ethene instead of tetrakis(p-hydroxyphenyl)methane and isocyanatoethyl acrylate instead of methacryloyl oxyethyl isocyanate.

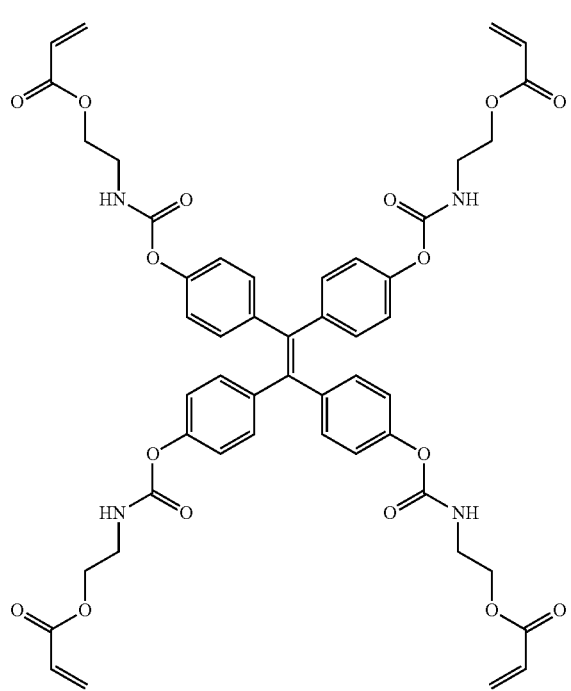

Example 9

Synthesis of Compound of Chemical Formula I

A compound of the following Chemical Formula I ($^1$H NMR (300 MHz, CDCl$_3$) δ 8.03 (t NH), 7.0-7.2 (d 8H), 7.2-7.4 (d 8H), 6.27, 5.59 (s C=CH$_2$), 6.05 (s 4H), 4.71 (s CH$_2$), 1.57 (s CH$_3$)) is prepared according to the same method as in Example 1, except for using tetrakis(p-hydroxyphenyl)ethene instead of tetrakis(p-hydroxyphenyl)methane and 1,1-bis(acryloyloxymethyl)ethyl isocyanate instead of methacryloyl oxyethyl isocyanate.

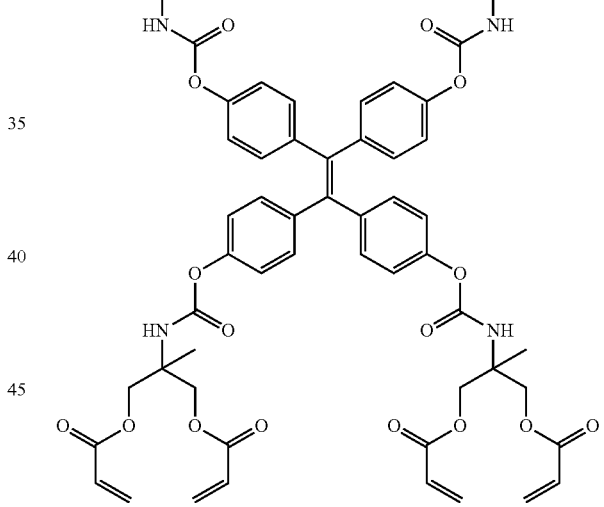

Example 10

Synthesis of a Compound of Chemical Formula J

A compound of the following Chemical Formula J ($^1$H NMR (300 MHz, CDCl$_3$) δ 8.22 (t NH) δ 6.1-7.3 (d 6H), 7.3-7.5 (d 6H), 6.48, 6.40 (s C=CH$_2$), 4.58 (t CH$_2$), 3.15 (t CH$_2$), 0.66 (s CH$_3$)) is prepared according to the same method as in Example 1, except for using 1,1,1-(4-hydroxyphenyl)silane instead of tetrakis(p-hydroxyphenyl)methane.

J

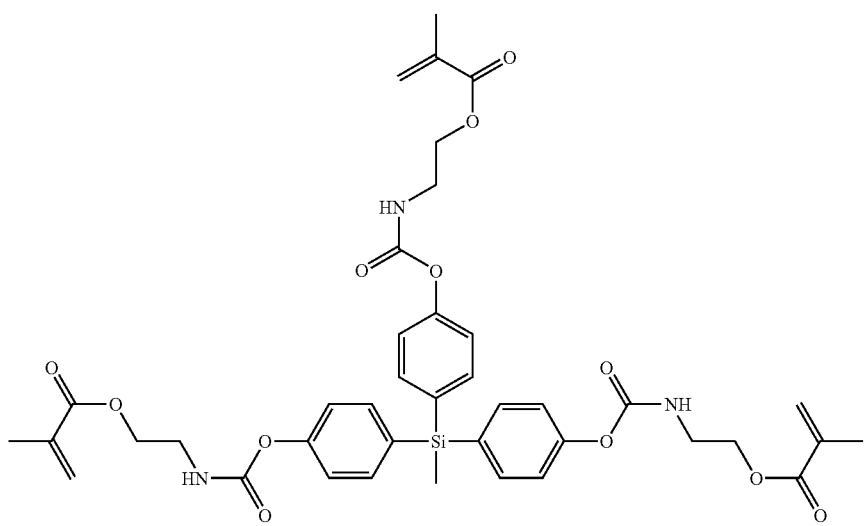

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A compound represented by the following Chemical Formula 2:

[Chemical Formula 2]

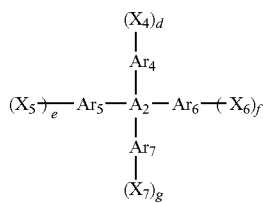

wherein, in the above Chemical Formula 2, $A_2$ is carbon (C) or silicon (Si), $Ar_4$ to $Ar_7$ are the same or different and are independently a substituted or unsubstituted C6 to C20 arylene, $X_4$ to $X_7$ are the same or different and are independently selected from the group consisting of hydrogen, a C1 to C5 alkyl, substituents represented by the Chemical Formula 1-1 and substituents represented by the following Chemical Formula 1-2, provided that at least one of $X_4$ to $X_7$ is selected from the group consisting of substituents represented by the above Chemical Formula 1-1 and substituents represented by the following Chemical Formula 1-2, and d to g are independently integers of 1 or 2, and when d to g are each equal to 2, each of $X_4$ to $X_7$ are the same or different;

[Chemical Formula 1-1]

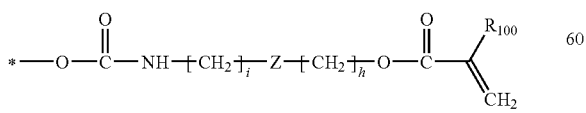

wherein, in above Chemical Formula 1-1, Z is selected from the group consisting of a single bond, —O—, —COO—, and —OCO—, i is an integer ranging from 1 to 5, h is an integer ranging from 0 to 5, and $R_{100}$ is hydrogen or a methyl, provided that when Z is —O—, —COO—, or —OCO—, h is not zero (0),

[Chemical Formula 1-2]

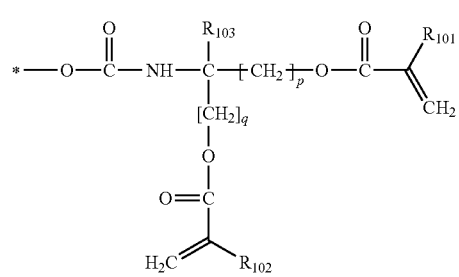

wherein, in the above Chemical Formula 1-2, p and q are independently integers ranging from 1 to 5, and $R_{101}$ to $R_{103}$ are independently hydrogen or a methyl.

2. The compound of claim 1, wherein the compound of the above Chemical Formula 2 includes a compound represented by Chemical Formula 2A:

[Chemical Formula 2A]

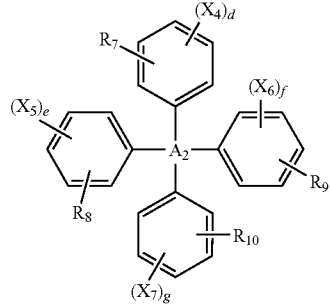

wherein, in the above Chemical Formula 2A, $A_2$ is carbon (C) or silicon (Si), $R_7$ to $R_{10}$ and $X_4$ to $X_7$ are the same or different and are independently selected from the group consisting of hydrogen, a C1 to C5 alkyl, substituents represented by the above Chemical Formula 1-1 and substituents represented by the following Chemical Formula 1-2, provided that at least one of $R_7$ to $R_{10}$ and $X_4$ to $X_7$ is selected from the group consisting of substituents represented by the above Chemical Formula 1-1 and substituents represented by the following Chemical Formula 1-2, and d to g are independently integers of 1 or 2, and when d to g are each equal to 2, each of $X_4$ to $X_7$ are the same or different.

3. The compound of claim 1, wherein at least three of $X_4$ to $X_7$ in the above Chemical Formula 2 are substituents represented by the Chemical Formula 1-1 and substituents represented by the following Chemical Formula 1-2.

4. The compound of claim 1, where the compound is used in an adhesive composition, a photocurable paint and ink composition, a light guide, an insulation layer, an optical filter, a flame retardant resin or in a plastic optical fiber.

* * * * *